United States Patent [19]

Hunter

[11] 4,349,450
[45] Sep. 14, 1982

[54] CATALYTIC ELEMENTS

[75] Inventor: James B. Hunter, Newton Square, Pa.

[73] Assignee: Johnson Matthey, Inc., Malvern, Pa.

[21] Appl. No.: 249,873

[22] Filed: Apr. 1, 1981

[51] Int. Cl.$^3$ .................... B01J 21/04; B01J 23/40; B01J 35/04

[52] U.S. Cl. .................... 252/466 PT; 252/477 R

[58] Field of Search .................... 252/466 PT, 477 R

[56] References Cited

U.S. PATENT DOCUMENTS

| | | | |
|---|---|---|---|
| 2,602,651 | 7/1952 | Cannon | 261/95 |
| 3,362,783 | 1/1968 | Leak | 423/212 |
| 3,876,555 | 4/1975 | Mikhailovich et al. | 252/477 R |
| 4,152,302 | 5/1979 | Nonnenmann et al. | 252/477 R |
| 4,162,993 | 7/1979 | Retallick | 252/477 R |
| 4,196,099 | 4/1980 | Hunter et al. | 252/437 |

*Primary Examiner*—W. J. Shine
*Attorney, Agent, or Firm*—Cushman, Darby & Cushman

[57] ABSTRACT

A catalytic element comprising small, thin-walled metal half-cylinders, slightly tapered at one end and perforated to give a large number of generally frusto-conical projections over the entire outer surface. The outer ends of the projections are jagged or burred. A wide variety of active catalytic materials can be applied to the entire surface of these metal members for use in a wide variety of gas and liquid phase reactions.

3 Claims, 3 Drawing Figures

CATALYTIC ELEMENTS

This invention relates to catalytic elements for promoting chemical reactions and to chemical reactions promoted by such elements. In particular, the invention relates to catalytic elements of special shape and structure which result in high catalytic activity and in otherwise good performance during use in carrying out chemical reactions.

BACKGROUND AND PRIOR ART

Beds of discrete, randomly-arranged catalytic elements are frequently employed to promote chemical reactions. Such discrete catalytic elements have been used in a wide variety of geometric shapes, including spheres, rings, saddles, coils, cork screws, triangles, curlicues, rods, pellets, powders, extrudates and the like. The elements may themselves be catalytic or they may serve as a support, substrate or carrier for a catalytic material.

As examples of metal supports for catalytic material reference may be had to U.S. Pat. Nos. 3,994,831 and 2,974,150. U.S. Pat. No. 3,994,831 discloses a catalyst support formed in the shape of a perforated metal Leesing ring, i.e. a closed perforated cylinder which is bisected by a perforated surface. In one example according to the patent, a packed bed of such rings, made of a chromium-aluminum-iron alloy and coated with a mixture of platinum and palladium as a catalytically active material, is contacted by an ethylene-containing waste gas stream to convert the ethylene to carbon dioxide and water. U.S. Pat. No. 2,974,150 discloses a catalyst support in the form of a silver or stainless steel element having bonded thereto a silver-alkaline earth metal alloy as a catalytically active material. The coated elements in the form of a bed are useful in converting ethylene to ethylene oxide when the bed is contacted by a gaseous reaction mixture containing ethylene and oxygen. The elements are illustrated as having the shape of plain rings, spirals, cork screws, triangles, curlicues or Lessing rings.

SUMMARY OF THE INVENTION

The present invention provides a catalytic element in the form of a thin-walled shaped metallic member having a plurality of hollow, generally frusto-conical or volcano-shaped projections on at least one surface, the outer ends of the projections being open and thereby forming perforations through the member. The metallic member may itself be catalytically active or a catalytically active material may be supported on all surfaces of the member, including the projections. Preferably the peripheries of the open outer ends of the projections are sharp, jagged, burred or frayed, as would result from forming the projections by piercing the thin metal wall with a die. When formed in this manner each perforation exhibits the burred projection extending from one surface of the metal sheet and a recess in the opposite surface.

Particularly suitable metal members for the catalytic elements of this invention are the distillation column packing units described in U.S. Pat. No. 2,602,651, the disclosure of which is incorporated herein by reference. The patent describes various shapes and sizes for the units, all of which are thin-walled and perforated so as to exhibit burred projections such as those described above. Of the several different shapes described in the patent, the preferred one for present purposes is a thin-walled, half-cylindrical shell, slightly tapered toward one end and having a large number of the previously-described projections extending outwardly from the outer surface. Such a structure is currently being sold by Scientific Development Co. of State College, Pennsylvania under the name Pro-Pak. The shells are formed from a thin metal ribbon, for example stainless steel, nickel or monel, of about 0.003–0.004" thickness through which a large number of tiny holes have been made by piercing with a die. As the die pushes through the metal from one side, jagged burrs are formed on the opposite side in surrounding relationship to each hole formed by the die. Currently available shells are those designated as the "0.16-inch" and "0.24-inch" sizes which are characterized by the following parameters wherein $D_1$, $D_2$, $L_1$ and $R_1$ represent the dimensions indicated in FIG. 1:

| Size | .016 × .016 | 0.24 × 0.24 |
| --- | --- | --- |
| $D_1$ | 4 mm | 6 mm |
| $D_2$ | 3 mm | 4.5 mm |
| $L_1$ | 4 mm | 6 mm |
| $R_1$ | 2.4 mm | 3.5 mm |
| No. of holes | 40 | 84 |
| Hole size | 0.2–0.3 mm | 0.2–0.3 mm |

As noted, the metal from which the members are made may itself be catalytic for some reactions. More typically, however, the metal member will form a support, substrate or carrier for a catalytic material thus providing greater flexibility with respect to the nature of the chemical reactions which can be promoted. Thus, the identity of the metal is not critical except that it must, of course, be selected with the chemical and physical aspects of the reaction environment in mind. Generally, metals having good resistance to heat and corrosion and having sufficient strength and hardness for the physical aspects of the reaction will be selected. Suitable support metals include, for example, nickel, monel, stainless steels and various other alloys such as nickel-chromium-iron, aluminum-chromium-iron and chromium-silicon-iron, typically "Kanthal" or "Fecralloy".

Similarly, the only restraints on the selection of the active catalytic material are those arising from the chemical and physical nature of the reaction environment. The catalytic material may thus be metallic or non-metallic and it may be applied to the support metal in any known manner. Catalytic metals include the rare earths, silver, titanium, manganese, copper, chromium, cadmium, molybdenum, vanadium, tungsten, rhenium, thorium, the noble metals such as the platinum group metals, and others. The catalytic material may be deposited and bonded to the support metal in any conventional way, as by impregnation and chemical decomposition, electroplating, dipping and so forth. If the catalytic metal is in powdered form it may be bonded to the support metal with high-temperature or solvent-resistant binders such as colloidal alumina, silica, aluminum phosphate or others. Non-metallic catalytic materials include various metal oxides, sulfides and the like. The catalytic material can also be applied over a substrate of high surface-area material which has been applied to the metal. Suitable substrate materials are, for example, alumina, silica, zirconia, titania and carbon blacks and graphite.

Essentially any chemical reaction which can be promoted by a solid catalyst can be carried out with the catalytic elements of this invention. Both gas phase and liquid phase reactions are contemplated. In the example described below a gas phase reaction is carried out between methane and carbon dioxide to produce carbon monoxide and hydrogen, by passing the gas mixture through a bed of the above-described half-cylindrical shells, each shell being a stainless steel member having a thin coating of alumina thereon and a second coating of ruthenium on the alumina. Other contemplated gas phase reactions are those carried out in gasoline reforming, ammonia synthesis, purification of exhaust gases from industrial process and from internal combustion engines and various oxidation processes such as the oxidation of ammonia and the oxidation of sulfur dioxide to sulfur trioxide.

An important liquid phase reaction which is promoted with the catalytic members is the hydrogenation of organic molecules in liquid solvents. In this case the catalytic material is usefully platinum or palladium or other platinum group metal carried on high surface area carbon powder bonded to the metal support member. Such reactions may be carried out in a trickle column reactor or in a high pressure autoclave where hydrogen gas is sparged into the stirred liquid in the presence of dispersed catalyst. In conventional autoclave hydrogenation, carbon-based catalysts in powder form must be removed by filtration and the liquid distilled or extracted to separate reaction products for recovery and purification. It frequently happens that some carbon catalysts that show high catalytic activity may exhibit poor filterability. The required filtration introduces a time consuming and costly step. Furthermore, the filter cake must be washed a number of times to recover valuable products that would otherwise be lost, thereby adding further time and cost. By attaching the carbon particles to the metal support members of the present invention the catalyst may be left in the autoclave and the liquid easily drained from the bottom through a screen. No product is lost and the catalyst can be used again for the next charge of feed. Thus, time and material are saved and the catalyst undergoes a minimum amount of physical degradation due to handling.

An important aspect of the present catalytic elements is the sharp or burred edge on each of the multipoint perforations, as such edges have been found to be areas of high catalytic activity in the sense that they promote "light off" in a reaction environment, particularly in the case of a gas phase reaction. That is, they are the first portions of the element to initiate the chemical reaction and thereafter the entire catalytic surface becomes active. The elements have, therefore, high catalytic activity and high conversion rates during use. Further, they exhibit high surface area yet low weight and low volume per unit area. This combination of features is particularly characteristic of the preferred tapered half-cylinders, because the taper prevents any substantial nesting of the elements yet does permit a minor amount of nesting which does not reduce the active surface area. These features are particularly important where it is desirable to place a bed of the elements in a reaction vessel which is elongated and of small transverse cross section. The elements also provide a remarkably low pressure drop per unit of bed length. It has been found, for example, that a bed made up of the present catalytic elements gives approximately 10% of the pressure drop encountered with a comparable bed of ceramic pellets. This is an extremely important advantage from the energy standpoint since the power required to pump large volumes of gas through a catalyst bed is substantial.

A further advantage of the invention is that beds of the elements show little or no channeling of the fluid passing through the beds. Furthermore, the thin walls of the elements promote rapid heat conduction during use, preventing hot spots and promoting a uniform bed temperature. Another advantage is ease of loading into reactors of complex shape, for example coiled tubes, while still forming a uniform bed which shows low pressure drop and absence of channeling.

DETAILED DESCRIPTION OF AN EXEMPLARY EMBODIMENT

Figure 1:
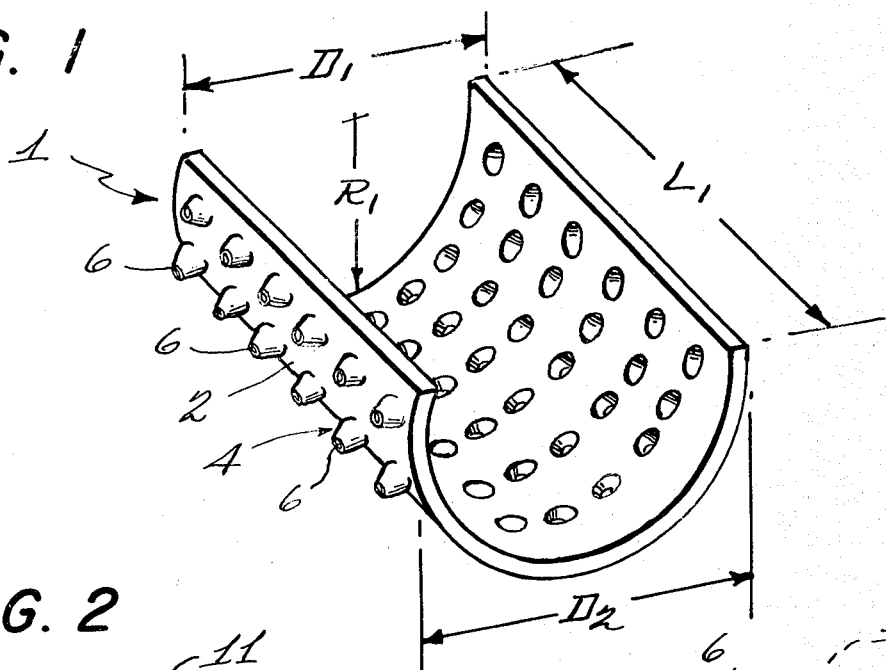
FIG. 1 is a perspective view of a preferred form of catalytic element according to the invention.
Figure 2:
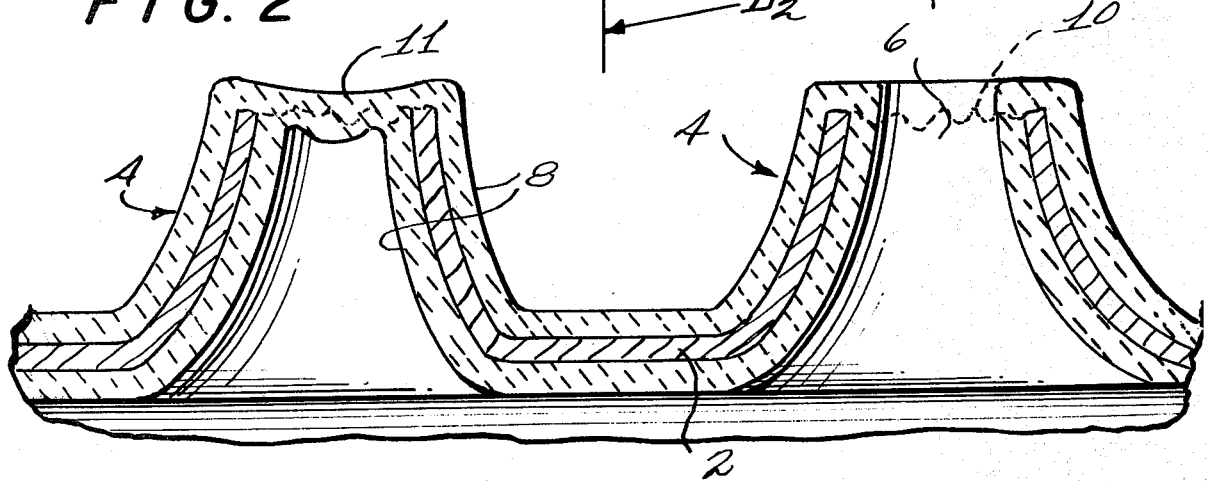
FIG. 2 is a sectional view, on an enlarged scale, of typical projections in the catalytic element.

As will be evident from FIGS. 1 and 2, the catalytic element (1) of the invention comprises a thin-walled shaped metallic (stainless steel) support member (2) which has a plurality of hollow, generally frusto-conical projections (4) on the outer surface and which is commercially available as "Pro-Pak". The support member (2), as best shown in FIG. 1, is a slightly tapered half cylinder. The outer ends of the projections (4) are open as shown at (6) so as to form perforations through the catalyst support. A coating of catalytic material (8), comprising an alumina washcoat impregnated with ruthenium metal, conventionally applied to the "Pro-Pak", covers the entire surface of the metal support member (2). The outer edge of each projection (4) is preferably jagged as illustrated by the broken lines (10) across the ends of the projections in FIG. 2. Also as shown in FIG. 2, the open ends of the projections (4) may be closed by the catalytic coating as shown at (11) or open.

Figure 3:
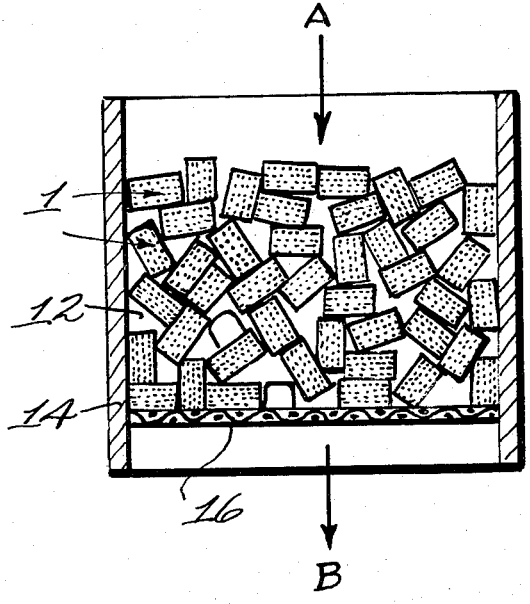
FIG. 3 is a schematic view illustrating a bed of the catalytic elements of FIG. 1.

FIG. 3 diagrammatically illustrates one way of using the catalytic element of FIG. 1 to catalyze a gas or liquid phase reaction. Thus, a bed (12) of the catalytic elements (1) is provided in reaction vessel (14) supported on a suitable screen (16), the reactant gas mixture being passed into the reaction vessel (14) as shown at (A) and the gaseous reaction product being taken out at (B). Alternatively, a liquid feed may be introduced at the top of the reaction (e.g. a trickle column) and hydrogen or other gas fed in at the bottom for reaction over the catalyst bed (12), reaction products being taken off in the effluent from the bottom of the reactor and at any convenient point (not shown).

One particular application using the present catalytic elements is as a catalyst for a solar energy conversion and storage system known as the "Solchem" process (see Popular Science, June 1980, pages 68-71). In this process, carbon dioxide and methane are catalytically reacted at about 900° C. and 75 psig pressure by passing a mixture of the gases in about a 3:1 mol ratio through a bed of the ruthenium/alumina/"Pro-Pak" catalytic elements (1) containing 0.4% ruthenium by weight, positioned in a "Kanthal" metal coil, the coil being located at the focus point of a large paraboloidal mirror where the coil can absorb concentrated solar radiation.

The solar radiation heats the catalyst and the gaseous reaction mixture to the desired temperature. As a result, an endothermic reaction takes place between the carbon dioxide and methane to give nearly complete conversion to carbon monoxide and hydrogen as represented by the following equation:

$$CH_4 + CO_2 \xrightarrow{catalyst} 2CO + 2H_2 \quad (1)$$
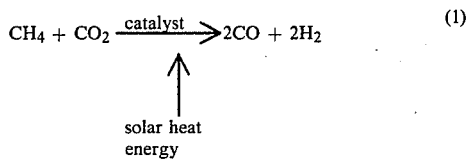

The reaction mixture of 2CO and $2H_2$ has a greater energy content (or enthalpy) than $CH_4$ and $CO_2$ by the amount of solar energy absorbed. The gas coming out of the coil containing this stored energy or enthalpy then flows through a pipe line to a power station where a second catalyst causes the reverse reaction to take place:

$$2CO + 2H_2 \xrightarrow{catalyst} CH_4 + CO_2 \quad (2)$$
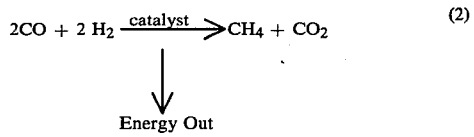

Because the mixture of $CH_4+CO_2$ has a lesser energy content (enthalpy) than the $2CO+2H_2$, heat is given off and may be exchanged to a working gas that drives a hot gas turbine which in turn drives an electric generator. Thus, solar energy absorbed at the focus of the paraboloidal mirror ends up as electricity from the generator.

The catalyst of the invention may be used for reactions (1) and (2).

As noted, the support member (2) used in the example given above is made of stainless steel. However, as noted earlier, other alloys may be used as catalyst supports herein.

It will be appreciated that the above-described use of the present catalyst in the Solchem system is given only for purposes of illustration as the present catalyst may be used in a wide variety of gas and liquid phase reactions. As a further example, a liquid phase hydrogenation catalyst is prepared by "washcoating" a mixture of high surface area carbon powder and aluminum phosphate binder onto the "Pro-pak" substrate. This combination is subsequently heat treated and catalyzed in conventional manner by impregnating with a palladium solution. The resulting catalyst may be used in either a trickle column or in a rotating basket autoclave for otherwise conventional hydrogenation.

I claim:

1. A catalytic element for promoting catalyzed chemical reactions comprising a thin-walled metallic member having a plurality of hollow generally frusto-conical projections on a surface thereof, and a catalytically active material supported on the surface of said members, wherein the metallic member is a half-cylindrical shell, slightly tapered toward one end and wherein the outer ends of the projections are slightly jagged, the catalytically active material being present on the entire surface of the element including the outer ends of the projections.

2. A catalytic member as in claim 1 wherein the catalytically active material comprises an alumina washcoat carrying a platinum group metal.

3. A method of preparing a supported catalyst for promoting chemical reactions comprising applying a catalytically active material to the entire surface of a support in the form of a thin-walled metallic member having a plurality of hollow generally frusto-conical projections wherein the peripheries of the projections are slightly jagged and wherein the catalytically active material is applied to the entire surface of the member including said projections.

* * * * *